United States Patent [19]

Hall et al.

[11] 4,081,483
[45] Mar. 28, 1978

[54] 1-(2-METHYL-2-PROPENYL)-3-(4-METHYL-3-PENTENYL)-$\Delta^3$-CYCLOHEXENE-1-CARBOXALDEHYDE AND 1-(2-METHYL-2-PROPENYL)-4-(4-METHYL-3-PENTENYL)-$\Delta^3$-CYCLOHEXENE-1-CARBOXALDEHYDE

[75] Inventors: John B. Hall, Rumson; Mark A. Sprecker, Sea Bright; Manfred Hugo Vock, Locust, all of N.J.; Edward J. Shuster, Brooklyn, N.Y.; Joaquin Vinals, Red Bank; Robert M. Novak, Fords, both of N.J.

[73] Assignee: International Flavors & Fragrances Inc., New York, N.Y.

[21] Appl. No.: 811,620

[22] Filed: Jun. 30, 1977

Related U.S. Application Data

[63] Continuation-in-part of Ser. No. 741,088, Nov. 11, 1976.

[51] Int. Cl.$^2$ .................................................... C07C 47/38
[52] U.S. Cl. ......................................... 260/598; 426/534; 252/522; 424/69
[58] Field of Search ...................................... 260/598

[56] References Cited

U.S. PATENT DOCUMENTS

| | | | |
|---|---|---|---|
| 2,842,598 | 7/1958 | Kitchens | 260/598 |
| 2,947,780 | 8/1960 | Teegarden et al. | 260/598 X |
| 3,929,895 | 12/1975 | Hall | 260/598 X |
| 3,981,924 | 9/1976 | Hall | 260/598 |

*Primary Examiner*—Bernard Helfin
*Attorney, Agent, or Firm*—Arthur L. Liberman; Franklin D. Wolffe

[57] ABSTRACT

Described are the compounds 1-(2-methyl-2-propenyl)-3-(4-methyl-3-pentenyl)-$\Delta^3$-cyclohexene-1-carboxaldehyde and 1-(2-methyl-2-propenyl)-4-(4-methyl-3-pentenyl)-$\Delta^3$-cyclohexene-1-carboxaldehyde; and a process for preparing same by means of reacting a methallylic halide with a mixture of 3 and 4-(4-methyl-3-pentenyl)-$\Delta^3$-cyclohexene-1-carboxaldehyde using a phase transfer agent in a two phase system according to the reaction:

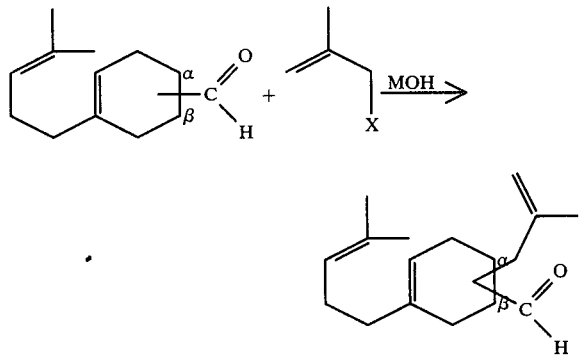

wherein the carboxaldehyde moiety is bonded to the alpha-carbon atom or the beta-carbon atom, X is chloro or bromo and M is alkali metal, processes for adding such 1-(2-methyl-2-propenyl)-(4-methyl-3-pentenyl)-$\Delta^3$-cyclohexene-1-carboxaldehydes to consumable materials whereby:

i. In foodstuffs and medicinal products, floral, muguet, coriander, fatty, green and creamy aroma and flavor characteristics are augmented or enhanced;

ii. In perfumes and perfumed articles, citrus, floral and fatty nuances are imparted, augmented and/or enhanced; and iii. In tobaccos and tobacco flavor and aroma imparting or enhancing compositions, sweet, spicey, coriander-like, citrus/fruity notes are imparted, prior to, and, on smoking and tobacco, foodstuff, flavor and perfume compositions containing the 1-(2-methyl-2-propenyl)-(4-methyl-3-pentenyl)-$\Delta^3$-cyclohexene-1-carboxaldehydes.

3 Claims, 2 Drawing Figures

FIG.2

IR SPECTRUM FOR EXAMPLE I

1-(2-METHYL-2-PROPENYL)-3-(4-METHYL-3-PENTENYL)-Δ³-CYCLOHEXENE-1-CARBOXALDEHYDE AND 1-(2-METHYL-2-PROPENYL)-4-(4-METHYL-3-PENTENYL)-Δ³-CYCLOHEXENE-1-CARBOXALDEHYDE

This applicaion is a continuation-in-part of U.S. Application for Letters Patent Ser. No. 741,088, filed on Nov. 11, 1976.

BACKGROUND OF THE INVENTION

The present invention provides the compounds 1-(2-methyl-2-propenyl)-3-(4-methyl-3-pentenyl)-Δ³-cyclohexene-1-carboxaldehyde and 1-(2-methyl-2-propenyl)-4-(4-methyl-3-pentenyl)-Δ³-cyclohexene-1-carboxaldehyde and a straight-forward, economical process directed towards synthesizing the 1-(2-methyl-2-propenyl)-(4-methyl-3-pentenyl)-Δ³-cyclohexene-1-carboxaldehydes by reaction of a methallylic halide with a mixture comprising 3-(4-methyl-3-pentenyl)-Δ³-cyclohexene-1-carboxaldehyde and 4-(4-methyl-3-pentenyl)-Δ³-cyclohexene-1-carboxaldehyde, also referred to as myrac aldehyde, having the structure:

and utilization of the 1-(2-methyl-2-propenyl)-(4-methyl-3-pentenyl)-Δ³-cyclohexene-1-carboxaldehydes for their organoleptic properties in perfumes, perfumed articles, foodstuffs, foodstuff flavoring compositions, tobaccos, tobacco flavoring compositions and medicinal products.

In the perfumery art there is a considerable need for substituents having citrus, floral and fatty nuances. Sweet, spicey, coriander-like and citrus/fruity notes are desirable in tobacco flavoring compositions. Specifically described are materials having such an organoleptic profile but which do not discolor with age. Such fragrance materials have a wide utilization in the presence of these perfume compounds. A limited amount of such materials that give rise to these properties is available from natural sources but the natural materials are subject to wide variations in quality, are expensive, and are often in critically short supply.

In addition, there is a continuing search for food flavor compositions which can vary, fortify, modify, enhance, augment or otherwise improve the flavor and aroma of foodstuffs and medicinal products. To be satisfactory, such compositions should be stable, non-toxic and blendable with other ingredients to provide its own unique flavor and aroma nuance without detracting from the co-ingredients. Preferably, such compositions should be naturally occurring or present in natural foodstuffs so that its ingestible safety can be readily recognized. These materials should be capable of being synthesized in a simple and economical manner. The need for safe flavors in the coriander area and dairy flavor area is well-known. More specifically, there is a need for the development of non-toxic materials which can replace natural materials not readily available, having creamy and coriander-like aromas and flavor characteristics.

The instant invention provides the foregoing, which the prior art has heretofore failed to provide. Furthermore, nothing in the prior art shows compounds having structures even remotely similar to the 1-(2-methyl-2-propenyl)-(4-methyl-3-pentenyl)-Δ³-cyclohexene-1-carboxaldehydes of the instant invention.

THE INVENTION

The present invention and mixtures of the compounds 1-(2-propenyl)-3-(4-methyl-3-pentenyl)-Δ³-cyclohexene-1-carboxaldehydes and 1-(2-methyl-2-propenyl)-4-(4-methyl-3-pentenyl)-Δ³-cyclohexene-1-carboxaldehydes having the generic structure:

wherein the carboxaldehyde moiety is bonded either at the alpha-carbon atom or the beta-carbon atoms of the cyclohexenyl moiety.

The compounds having the structures:

as well as the mixtures produced by the structure:

are each capable of augmenting or enhancing coriander-type and dairy flavors by providing therein or imparting thereto, floral, muguet, coriander, fatty, green and creamy aroma and flavor characteristics.

The compounds 1-(2-methyl-2-propenyl)-3-(4-methyl-3-pentenyl)-Δ³-cyclohexene-1-carboxaldehyde and 1-(2-methyl-2-propenyl)-4-(4-methyl-3-pentenyl)-Δ³-cyclohexene-1-carboxaldehyde are also capable of modifying or enhancing the odor characteristics of perfume compositions and perfumed articles by imparting thereto citrus, floral and fatty notes, thus fulfilling a need in the field of perfumery.

In tobacco and tobacco flavoring compositions the compounds 1-(2-methyl-2-propenyl)-(4-methyl-3-pentenyl)-Δ³-cyclohexene-1-carboxaldehyde and 1-(2-methyl-2-propenyl)-4-(4-methyl-3-pentenyl)-Δ³-cyclohexene-1-carboxaldehyde impart sweet, spicey, coriander-like, citrus/fruity notes.

The compounds 1-(2-methyl-2-propenyl)-3-(4-methyl-3-pentenyl)-Δ³-cyclohexene-1-carboxaldehyde and 1-(2-methyl-2-propenyl)-4-(4-methyl-3-pentenyl)-Δ³-cyclohexene-1-carboxaldehyde are produced by reacting myrac aldehyde having the structure:

with a methallylic halide in the presence of an inert solvent and an alkali metal hydroxide and in the presence of a "phase transfer agent". The reaction is carried out in a two-phase system. Thus, one aspect of our invention is illustrated in the following reaction:

wherein the carboxaldehyde moiety is bonded to the alpha-carbon atom or the beta-carbon atom, X is chloro or bromo and M is alkali metal.

One aspect of our invention involves the aforementioned process comprising the step of placing the reactants for the process and the base, respectively, in two immiscible phases; an organic phase and either (i) an aqueous base phase or (ii) a solid base phase with the reactants being located substantially entirely in the first mentioned organic phase and the base being located substantially entirely in the second mentioned phase; and adding to this two phase system a "phase transfer agent" which may be one or more of several organic quaternary ammonium salts.

Specific examples of phase transfer agents useful in our invention are as follows:

Quaternary Ammonium Salts

Tricapryl methyl ammonium chloride;
Cetyl trimethyl ammonium chloride;
Cetyl trimethyl ammonium bromide; and
Benzyl trimethyl ammonium hydroxide.

Tertiary Amines

Trimethylamine;
Triethylamine; and
Dimethyl (dimethyl amino ethyl) amine.

Crown Ethers

18-crown-6 having the structure:

and

Crown Ethers

Dibenzo-18-crown-6 having the structure:

In general, the phase transfer agents most preferred have the generic formula:

wherein at least one of $R_1$, $R_2$, $R_3$ and $R_4$ is $C_6$-$C_{14}$ aryl, $C_6$-$C_{10}$ aralkyl, $C_6$-$C_{20}$ alkyl, $C_6$-$C_{14}$ alkaryl and $C_6$-$C_{20}$ alkenyl and the other of $R_2$, $R_3$ and $R_4$ is alkyl such as methyl, ethyl, n-propyl, i-propyl, 1-butyl, 2-butyl, 1-methyl-2-propyl, 1-pentyl and 1-octyl and $Z^-$ is an anion such as chloride, bromide and hydroxide.

The process of our invention is carried out in an inexpensive solvent which is inert to the reaction system such as toluene, benzene, o-oxylene, m-xylene, p-xylene, ethyl benzene, n-hexane, cyclohexane, methylene chloride and o-dichlorobenzene.

The process of our invention is carried out at a temperature in the range of from about 10° C up to about 150° C with a temperature range of 50°-120° C being preferred. The reaction time is inversely proportional to the reaction temperature, with lower reaction temperatures giving rise to greater reaction times; and, accordingly, the reaction time ranges from about 30 minutes up to about 10 hours.

In the reaction of our invention the mole ratio of myrac aldehyde to the methallyl halide reactant is in the range of from 0.5:1.5 up to 1.5:0.5 with a preferred ratio being from 1:1 up to 1:1.2.

The mole ratio of base to methallylic halide in the reaction mass may be in the range of from about 0.75:1 up to about 1.5:1 with a preferred ratio of base:methallylic halide being from 1:1 up to 1.2:1.

The quantity of "phase transfer agent" in the reaction mass, based on the amount of myrac aldehyde in the reaction mass, may vary from 0.5 grams per mole of the myrac aldehyde up to 25 grams per mole, with a preferred concentration of "phase transfer agent" being in the range of from about 2.5 up to about 7.5 grams of "phase transfer agent" per mole of myrac aldehyde.

The reaction of our invention is preferably carried out at atmospheric pressure since that is the most convenient condition, however, lower or higher pressures can be used without detrimentally affecting the ultimate yield of desired reaction product.

The particular base used in the reaction is critical and, preferred are, sodium hydroxide and potassium hydroxide.

When the compound(s) 1-(2-methyl-2-propenyl)-(4-methyl-3-pentenyl)-$\Delta^3$-cyclohexene-1-carboxaldehydes of our invention are used as a food flavor adjuvant, the nature of the co-ingredients included with the compound(s) 1-(2-methyl-2-propenyl)-(4-methyl-3-pentenyl)-$\Delta^3$-cyclohexene-1-carboxaldehydes in formulating the product composition will also serve to alter, modify, augment or enhance the organoleptic characteristics of the ultimate foodstuff treated therewith.

As used herein in regard to flavors, the terms "alters", "modify" and "augment" in their various forms mean "supplying or imparting flavor character or note to otherwise bland, relatively tasteless substances or augmenting the existing flavor characteristic where a natural flavor is deficient in some regard or supplementing the existing flavor impression to modify its quality, character or taste".

The term "enhance" is used herein to mean the intensification of a flavor or aroma characteristic or note without the modification of the quality thereof. Thus, "enhancement" of a flavor or aroma means that the enhancement agent does not add any additional flavor note.

As used herein, the term "foodstuff" includes both solid and liquid ingestible materials which usually do, but need not, have nutritional value. Thus, foodstuffs include soups, convenience foods, beverages, dairy products, candies, chewing gums, vegetables, cereals, soft drinks, snacks and the like.

As used herein, the term "medicinal product" includes both solids and liquids which are ingestible non-toxic materials which have medicinal value such as cough syrups, cough drops, aspirin and chewable medicinal tablets.

The term "chewing gum" is intended to mean a composition which comprises a substantially water-insoluble, chewable plastic gum base such as chicle, or substitutes therefor, including jelutong, guttakay, rubber or certain comestible natural or synthetic resins or waxes. Incorporated with the gum base in admixture therewith may be plasticizers or softening agents, e.g., glycerine; and a flavoring composition which incorporates the compound(s) 1-(2-methyl-2-propenyl)-(4-methyl-3-pentenyl)-$\Delta^3$-cyclohexene-1-carboxaldehydes of our invention, and in addition, sweetening agents which may be sugars, including sucrose or dextrose and/or artificial sweeteners such as cyclamates or saccharin. Other optional ingredients may also be present.

Substances suitable for use herein as co-ingredients or flavoring adjuvants are well known in the art for such use, being extensively described in the relevant literature. It is a requirement that any such material be "ingestibly" acceptable and thus non-toxic and otherwise non-deleterious particularly from an organoleptic standpoint, whereby the ultimate flavor and/or aroma of the consumable material used is not caused to have unacceptable aroma and taste nuances. Such materials may in general be characterized as flavoring adjuvants or vehicles comprising broadly stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxy-anisole (mixture of 2- and 3-tertiary-butyl-4-hydroxy-anisole), butylated hydroxy toluene (2,6-di-tertiary-butyl-4-methyl phenol), propyl gallate and the like and sequestrants, e.g., citric acid.

Thickener compounds include carriers, binders, protective colloids, suspending agents, emulsifiers and the like, e.g., agar agar, carrageenan; cellulose and cellulose derivatives such as carboxymethyl cellulose and methyl cellulose; natural and synthetic gums such as gum arabic, gum tragacanth; gelatin, proteinaceous materials; lipids; carbohydrates; starches, pectins, and emulsifiers, e.g., mono- and diglycerides of fatty acids, skim milk powder, hexoses, pentoses, disaccharides, e.g., sucrose corn syrup and the like.

Surface active agents include emulsifying agents, e.g., fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phospate, citric acid, lactic acid, vinegar and the like; colorants, e.g., carminic acid, cochineal, tumeric and curcuma and the like; firming agents such as aluminum sodium sulfate, calcium chloride and calcium gluconate; texturizers, anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, alpha-methyl-butyric acid, propionic acid, valeric acid, 2-methyl-2-pentenoic acid, and 2-methyl-3-pentenoic acid; ketones and aldehydes, e.g., acetaldehyde, acetophenone, acetone, acetyl methyl carbinol, acrolein, n-butanal, crotonal, diacetyl, 2-methyl butanal, beta, beta-dimethyl-acrolein, methyl-n-amyl ketone, n-hexenal, 2-hexenal, isopentanal, hydrocinnamic aldehyde, cis-3-hexenal, 2-heptanal, nonyl aldehyde, 4-(p-hydroxyphenyl)-2-butanone, alpha-ionone, beta-ionone, methyl-3-butanone, benzaldehyde, damascone, damascenone, acetophenone, 2-heptanone, o-hydroxyacetophenone, 2-methyl-2-hepten-6-one, 2-octanone, 2-undecanone, 3-phenyl-4-pentenal, 2-phenyl-2-hexenal, 2-phenyl-2-pentenal, furfural, 5-methyl furfural, cinnamaldehyde, beta-cyclohomocitral, 2-pentanone, 2-pentenal and propanal; alcohols such as 1-butanol, benzyl alcohol, 1-borneol, trans-2-buten-1-ol, ethanol, geraniol, 1-hexanal, 2-heptanol, trans-2-hexenol-1, cis-3-hexen-1-ol, 3-methyl-3-buten-1-ol, 1-pentanol, 1-penten-3-ol, p-hydroxyphenyl-2-ethanol, isoamyl alcohol, isofenchyl alcohol, phenyl-2-ethanol, alpha-terpineol, cis-terpineol hydrate, eugenol, linalool, 2-heptanol, acetoin; esters, such as butyl acetate, ethyl acetate, ethyl acetoacetate, ethyl benzoate, ethyl butyrate, ethyl caprate, ethyl caproate, ethyl caprylate, ethyl cinnamate, ethyl crotonate, ethyl formate, ethyl isobutyrate, ethyl isovalerate, ethyl laurate, ethyl myristate, ethyl alpha-methylbutyrate, ethyl propionate, ethyl salicylate, trans-2-hexenyl acetate, hexyl acetate, 2-hexenyl butyrate, hexyl butyrate, isoamyl acetate, isopropyl butyrate, methyl acetate, methyl butyrate, methyl caproate, methyl isobutyrate, alpha-methylphenylglycidate, ethyl succinate, isobutyl cinnamate, cinnamyl formate, methyl cinnamate and terpenyl acetate; hydrocarbons such as dimethyl naphthalene, dodecane, methyl diphenyl, methyl napthalene, myrcene, naphthalene, octadecane, tetradecane, tetramethyl naphthalene, tridecane, trimethyl naphthalene, undecane, caryophyllene, 1-phellandrene, p-cymene, 1-alphapinene; pyrazines such as 2,3-dimethylpyrazine, 2,5-dimethylpyrazine, 2,6-dimethylpyrazine, 3-ethyl-2,5-dimethylpyrazine, 2-ethyl-3,5,6-trimethylpyrazine, 3-isoamyl-2,5-dimethylpyrazine, 5-isoamyl-2,3-dimethylpyrazine, 2-isoamyl-3,5,6-trimethylpyrazine, isopropyl dimethylpyrazine, methyl ethylpyrazine, tetramethylpyrazine, trimethylpyrazine; essential oils, such as jasmine absolute, cassia oil, cinnamon bark oil, rose absolute, orris absolute, lemon essential oil, Bulgarian rose, yara yara and vanilla; lactones such as δ-nonalactone, δ-decalactone, δ-undecalactone, γ-nonalactone, γ-decalactone and γ-undecalactone; sulfides, e.g., methyl sulfide and other materials such as maltol, acetoin and acetals (e.g., 1,1-diethoxyethane, 1,1-dimethoxyethane and dimethoxymethane).

The specific flavoring adjuvant selected for use may be either solid or liquid depending upon the desired physical form of the ultimate product, i.e., foodstuff, whether simulated or natural, and should, in any event, (i) be organoleptically compatible with the compound(s) 1-(2-methyl-2-propenyl)-(4-methyl-3-pentenyl)-$\Delta^3$-cyclohexene-1-carboxaldehydes of our invention by not covering or spoiling the organoleptic properties (aroma and/or taste) thereof; (ii) be non-reactive with the compound(s) 1-(2-methyl-2-propenyl)-(4-methyl-3-pentenyl)-$\Delta^3$-cyclohexene-1-carboxaldehydes of our invention and (iii) be capable of providing an environment in which the compound(s) 1-(2-methyl-2-propenyl)-(4-methyl-3-pentenyl)-$\Delta^3$-cyclohexene-1-carboxaldehydes can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff, chewing gum, medicinal product or toothpaste to which the flavor and/or aroma are to be imparted, modidifed, altered or enhanced. In contradistinction, in the preparation of solid products, e.g., simulated foodstuffs, ingredients capable of providing normally solid compositions should be selected such as various cellulose derivatives.

As will be appreciated by those skilled in the art, the amount of the 1-(2-methyl-2-propenyl)-(4-methyl-3-pentenyl)-$\Delta^3$-cyclohexene-1-carboxaldehydes employed in a particular instance can vary over a relatively wide range, depending upon the desired organoleptic effects to be achieved. Thus, correspondingly, greater amounts would be necesarry in those instances wherein the ultimate food composition to be flavored is relatively bland to the taste, whereas relatively minor quantities may suffice for purposes of enhancing the composition merely deficient in natural flavor or aroma. The primary requirement is that the amount selected to be effective, i.e., sufficient to alter, modify or enhance the organoleptic characteristics of the parent composition, whether foodstuff per se, chewing gum per se, medicinal product per se, toothpaste per se, or flavoring composition.

The use of insufficient quantities of the compound(s) 1-(2-methyl-2-propenyl)-(4-methyl-3-pentenyl)-$\Delta^3$-cyclohexene-1-carboxaldehydes will, of course, substantially vitiate any possibility of obtaining the desired results while excess quantities prove needlessly costly and in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, chewing gum compositions, medicinal product compositions and toothpaste compositions, it is found that quantities of the compound(s) 1-(2-methyl-2-propenyl)-(4-methyl-3-pentenyl)-$\Delta^3$-cyclohexene-1-carboxaldehydes ranging from a small but effective amount, e.g., 0.5 parts per million up to about 100 parts per million based on total composition are suitable. Concentrations in excess of the maximum quantity stated are not normally recommended, since they fail to prove commensurate enhancement of organoleptic properties. In those instances, wherein the compound(s) 1-(2-methyl-2-propenyl)-(4-methyl-3-pentenyl)-$\Delta^3$-cyclohexene-1-carboxaldehydes is added to the foodstuff as an integral component of a flavoring composition, it is, of course, essential that the total quantity of flavoring composition employed be sufficient to yield an effective concentration of the 1-(2-methyl-2-propenyl)-(4-methyl-3-pentenyl)-$\Delta^3$-cyclohexene-1-carboxaldehydes in the foodstuff product.

Food flavoring compositions prepared in accordance with the present invention preferably contain the compound(s) 1-(2-methyl-2-propenyl)-(4methyl-3-pentenyl)-$\Delta^3$-cyclohexene-1-carboxaldehydes in concentrations ranging from about 0.1% up to about 15% by weight based on the total weight of the said flavoring composition.

The composition described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the compound(s) 1-(2-methyl-2-propenyl)-(4-methyl-3-pentenyl)-$\Delta^3$-cyclohexene-1-carboxaldehydes with, for example, gum arabic, gum tragacanth, carrageenan and the like, and thereafter spray-drying the resultant mixture whereby to obtain the particular solid product. Pre-prepared flavor mixes in powder form, e.g., a fruit-flavored powder mix are obtained by mixing the dried solid components, e.g., starch, sugar and the like and the compound(s) 1-(2-methyl-2-propenyl)-(4-methyl-3pentenyl)-$\Delta^3$-cyclohexene-1-carboxaldehydes in a dry blender until the requisite degree of uniformity is achieved.

it is presently preferred to combine with the compound(s) 1-(2-methyl-2propenyl)-(4-methyl-3-pentenyl)-Δ³-cyclohexene-1-carboxaldehydes of our invention, the following adjuvants:

p-Hydroxybenzyl acetone;
Geraniol;
Cassia Oil;
Acetaldehyde;
Maltol;
Ethyl methyl phenyl glycidate;
Benzyl acetate;
Dimethyl sulfide;
Eugenol;
Vanillin;
Caryophyllene;
Methyl cinnamate;
Guiacol;
Ethyl pelargonate;
Cinnamaldehyde;
Methyl anthranilate;
5-Methyl furfural;
Isoamyl acetate;
Isobutyl acetate;
Cuminaldehyde;
Alpha ionone;
Cinnamyl formate;
Ethyl butyrate;
Methyl cinnamate;
Acetic acid;
Gamma-undecalactone;
δ-decalactone;
Naphthyl ethyl ether;
δ-undecalactone;
Diacetyl;
Oil of Coriander;
Furfural;
Oil of Nutmeg;
Ethyl acetate;
Anethole;
2,3-Dimethyl pyrazine;
2-Ethyl-3-methyl pyrazine;
3-Phenyl-4-pentenal;
2-Phenyl-2-hexenal;
2-Phenyl-2pentenal;
3-Phenyl-4pentenal diethyl acetal;
Damascone (1-crotonyl-2,2,6-trimethylcyclohex-1one);
Damascenone (1-crotonyl-2,2,6-trimethylcyclohexa-1,5-diene);
Beta-cyclohomocitral (2,2,6-trimethylcyclohex-1-ene carboxaldehyde);
Isoamyl butyrate;
Cis-3-hexenol-1;
2-Methyl-2-pentenoic acid;
Elemecine (4-allyl-1,2,6-trimethoxy benzene);
Isoelemecine (4-propenyl-1,2,6-trimethoxy benzene); and
2-(4-Hydroxy-4-methylpentyl) norbornadiene (prepared according to U.S. Application for Letters Patent Ser. No. 461,703, filed on Apr. 17, 1974).

The compound(s) 1-(2-methyl-2-propenyl)-(4-methyl-3-pentenyl)-Δ³-cyclohexene-1-carboxaldehyde(s) and one or more auxiliary perfume ingredients, including, for example, alcohols, aldehydes, ketones, terpinic hydrocarbons, nitriles, esters, lactones, natural essential oils and synthetic essential oils, may be admixed so that the combined odors of the individual components produce a pleasant and desired fragrance, particularly and preferably in rose fragrances. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling fresh smelling materials.

In perfume compositions, it is the individual components which contribute to their particular olfactory characteristics, however the over-all sensory effect of the perfume composition will be at least the sum total of the effects of each of the ingredients. Thus, the compound(s) 1-(2-methyl-2-propenyl)-(4-methyl-3-pentenyl)-Δ³-cyclohexene-1-carboxaldehyde(s) can be used to alter, modify or enhance the aroma characteristics of a perfume composition, for example, by utilizing or moderating the olfactory reaction contributed by another ingredient in the composition.

The amount of the 1-(2-methyl-2-propenyl)-(4-methyl-3-pentenyl)-Δ³-cyclohexene-1-carboxaldehyde(s) of our invention which will be effective in perfume compositions as well as in perfumed articles and colognes depends on many factors, including the other ingredients, their amounts and the effects which are desired. It has been found that perfume compositions containing as little as 0.01% of the 1-(2-methyl-2-propenyl)-(4-methyl-3-pentenyl)-Δ³-cyclohexene-1-carboxaldehyde(s) or even less (e.g., 0.005%) can be used to impart citrus/fruity, floral nuances to soaps, cosmetics or other products. The amount employed can range up to 70% of the fragrance components and will depend on considerations of cost, nature of the end product, the effect desired on the finished product and the particular fragrance sought.

The compound(s) 1-(2-methyl-2-propenyl)-(4-methyl-3-pentenyl)-Δ³-cyclohexene-1-carboxaldehyde(s) of our invention is useful (taken alone or together with other ingredients in perfume compositions) as (an) olfactory component(s) in detergents and soaps, space odorants and deodorants, perfumes, colognes, toilet water, bath preparations, such as lacquers, brilliantines, pomades and shampoos; cosmetic preparations, such as creams, deodorants, hand lotions and sun screens; powders, such as talcs, dusting powders, face powders and the like. When used as (an) olfactory component(s) as little as 1% of the 1-(2-methyl-2-propenyl)-(4-methyl-3-pentenyl)-Δ³-cyclohexene-1-carboxaldehyde(s) will suffice to impart an intense floral note to rose formulations. Generally, no more than 3% of the 1-(2-methyl-2-propenyl)-(4-methyl-3-pentenyl)-Δ³-cyclohexene-1-carboxaldehyde(s), based on the ultimate end product, is required in the perfume composition.

In addition, the perfume composition or fragrance composition of our invention can contain a vehicle, or carrier for the compound(s) 1-(2-methyl-2-propenyl)-(4-methyl-3-pentenyl)-Δ³-cyclohexene-1-carboxaldehyde(s). The vehicle can be a liquid such as an alcohol, a non-toxic alcohol, a non-toxic glycol, or the like. The carrier can also be an absorbent solid, such as a gum (e.g., gum arabic) or components for encapsulating the composition (such as gelatin).

It will thus be apparent that the compound(s) 1-(2-methyl-2-propenyl)-(4-methyl-3-pentenyl)-Δ³-cyclohexene-1-carboxaldehyde(s) of our invention can be utilized to alter, modify or enhance sensory properties, particularly organoleptic properties, such as flavor(s) and/or fragrance(s) of a wide variety of consumable materials.

Furthermore, the 1-(2-methyl-2-propenyl)-(4-methyl-3-pentenyl)-$\Delta^3$-cyclohexene-1-carboxaldehydes of our invention are capable of supplying and/or potentiating certain flavor and aroma notes usually lacking in many tobacco flavors heretofore provided.

As used herein in regard to tobacco flavors, the terms "alter" and "modify" in their various forms mean "supplying or imparting flavor character or note to otherwise bland tobacco, tobacco substitutes, or tobacco flavor formulations or augmenting the existing flavor characteristic where a natural flavor is deficient in some regard or supplementing the existing flavor impression to modify its quality, character or taste".

As used herein, the term "enhance" is intended to mean the intensification (without change in kind of quality of aroma or taste) of one or more taste and/or aroma nuances present in the organoleptic impression of tobacco or a tobacco substitute or a tobacco flavor.

Our invention thus provides an organoleptically improved smoking tobacco product and additives therefor, as well as methods of making the same which overcome specific problems heretofore encountered in which specific desired coriander, citrus and spicey flavor characteristics are created or enhanced and may be readily controlled and maintained at the desired uniform level regardless of variations in the tobacco components of the blend.

This invention further provides improved tobacco additives and methods whereby various sweet, spicey, coriander-like, citrus/fruity notes may be imparted to smoking tobacco products and may be readily varied and controlled to produce the desired uniform flavor characteristics.

In carrying out this aspect of our invention, we add to smoking tobacco materials or a suitable substitute therefor (e.g., dried lettuce leaves) an aroma and flavor additive containing as an active ingredient the 1-(2-methyl-2-propenyl)-(4-methyl-3-pentenyl)-$\Delta^3$-cyclohexene-1-carboxaldehyde(s).

In addition to the 1-(2-methyl-2-propenyl)-(4-methyl-3-pentenyl)-$\Delta^3$-cyclohexene-1-carboxaldehyde(s) of our invention other flavoring and aroma additives may be added to the smoking tobacco materials or substitute therefor either separately or in mixture with the 1-(2-methyl-2-propenyl)-(4-methyl-3-pentenyl)-$\Delta^3$-cyclohexene-1-carboxaldehyde(s) as follows:

I. Synthetic Materials:

Beta-ethyl-cinnamaldehyde;
Eugenol;
Dipentene;
Damascenone;
Maltol;
Ethyl Maltol;
Delta undecalactone;
Delta decalactone;
Benzaldehyde;
Amyl acetate;
Ethyl butyrate;
Ethyl valerate;
Ethyl acetate;
Beta-cyclohomocitral;
2-Methyl-5-isopropyl-1,3-nonadiene-8-one;
2-Hexenol-1;
2,6-Dimethyl-2,6-undecadiene-10-one;
2-Methyl-5-isopropyl acetophenone;
2-Hydroxy-2,5,5,8a-tetramethyl-1-(2-hydroxyethyl)-decahydronaphthalene;
Dodecahydro-3a,6,6,9a-tetramethylnaphtho-(2,1-b)-furan;
4-Hydroxy hexanoic acid, gamma lactone,
Polyisoprenoid hydrocarbons defined in Example V of U.S. Pat. No. 3,589,372 issued on June 29, 1971.

II. Natural Oils

Celery seed oil;
Coffee extract;
Bergamot oil;
Cocoa extract;
Nutmeg oil;
Origanum oil.

An aroma and flavoring concentrate containing the 1-(2-methyl-2-propenyl)-(4-methyl-3-pentenyl)-66 $\Delta^3$-cyclohexene-1-carboxaldehyde(s) and, if desired, one or more of the above indicated additional flavoring additives may be added to the smoking tobacco material, to the filter or to the leaf or paper wrapper. The smoking tobacco material may be shredded, cured, cased and blended tobacco material or reconstituted tobacco material or tobacco substitutes (e.g., lettuce leaves) or mixtures thereof. The proportions of flavoring additives may be varied in accordance with taste but insofar as enhancement or the imparting of natural and/or sweet notes, we have found that satisfactory results are obtained if the proportion by weight of the sum total of the 1-(2-methyl-2-propenyl)-(4-methyl-3-pentenyl)-$\Delta^3$-cyclohexene-1-carboxaldehyde(s) to smoking tobacco material is between 250 ppm and 1,500 ppm (0.025%–.15%) of the active ingredients to the smoking tobacco material. We have further found that satisfactory results are obtained if the proportion by weight of the sum total of the 1-(2-methyl-2-propenyl)-(4-methyl-3-pentenyl)-$\Delta^3$-cyclohexene-1-carboxaldehyde(s) used to flavoring material is between 2,500 and 10,000 ppm (0.25%–1.5%).

Any convenient method for incorporating the 1-(2-methyl-2-propenyl)-(4-methyl-3pentenyl)-$\Delta^3$-cyclohexene-1-carboxaldehyde(s) in the tobacco product may be employed. Thus, the 1-(2-methyl-2-propenyl)-(4-methyl-3-pentenyl)-$\Delta^3$-cyclohexene-1-carboxaldehyde(s) taken alone or along with other flavoring additives may be dissolved in a suitable solvent such as ethanol, pentane, diethyl ether and/or other volatile organic solvents and the resulting solution may either be sprayed on the cured, cased and blended tobacco material or the tobacco material may be dipped into such solution. Under certain circumstances, a solution of the 1-(2-methyl-2-propenyl)-(4-methyl-3-pentenyl)-$\Delta^3$-cyclohexane-1-carboxaldehyde(s) taken alone or taken further together with other flavoring additives as set forth above, may be applied by means of a suitable applicator such as brush or roller on the paper or leaf wrapper for the smoking product, or it may be applied to the filter by either spraying, or dipping, or coating.

Furthermore, it will be apparent that only a portion of the tobacco or substitute therefor need be treated and the thus treated tobacco may be blended with other tobaccos before the ultimate tobacco product is formed. In such cases, the tobacco treated may have the 1-(2-methyl-2-propenyl)-(4-methyl-3-pentenyl)-$\Delta^3$- cyclohexene-1-carboxaldehyde(s) in excess of the amounts or concentrations above indicated so that when blended with other tobaccos, the final product will have the percentage within the indicated range.

In accordance with one specific example of our invention, an aged, cured and shredded domestic burley tobacco is sprayed with a 20% ethyl alcohol solution of the 1-(2-methyl-2-propenyl)-(4-methyl-3-pentenyl)-$\Delta^3$-cyclohexene-1-carboxaldehyde(s) in an amount to provide a tobacco composition containing 800 ppm by weight of the 1-(2-methyl-2-propenyl)-(4-methyl-3-pentenyl)-$\Delta^3$-cyclohexane-1-carboxaldehyde(s) on a dry basis. Thereafter, the alcohol is removed by evaporation and the tobacco is manufactured into cigarettes by the usual techniques. The cigarette when treated as indicated has a desired and pleasing aroma (increased smoke body sensation in the mouth with enhanced tobacco-like notes and pleasant aromatic nuances) which is detectable in the main and side streams when the cigarette is smoked. This aroma is described as having increased body, more tobacco-like, more aromatic, with spicey/coriander-like notes.

While our invention is particularly useful in the manufacture of smoking tobacco, such as cigarette tobacco, cigar tobacco and pipe tobacco, other tobacco products formed from sheeted tobacco dust or fines may also be used. Likewise, the 1-(2-methyl-2-propenyl)-(4-methyl-3-pentenyl)-$\Delta^3$-cyclohexene-1-carboxaldehyde(s) of our invention can be incorporated with materials such as filter tip materials, seam paste, packaging materials and the like which are used along with tobacco to form a product adapted for smoking. Furthermore, the 1-(2-methyl-2-propenyl)-(4-methyl-3-pentenyl)-$\Delta^3$-cyclohexane-1-carboxaldehyde(s) can be added to certain tobacco substitutes of natural or synthetic origin (e.g., dried lettuce leaves) and, accordingly, by the term "tobacco" as used throughout this specification is meant any composition intended for human consumption by smoking or otherwise, whether composed of tobacco plant parts or substitute materials or both.

The following examples serve to illustrate our invention and the invention is to be considered restricted thereto only as indicated in the appended claims.

All parts and percentages given herein are by weight unless otherwise specified.

EXAMPLE I

PREPARATION OF 1-METHALLYL-4-(4-METHYL-3-PENTENYL)-3-CYCLOHEXENE-1-CARBOXALDEHYDE AND 1-METHALLYL-3-(3-METHYL-3-PENTENYL)-3-CYCLOHEXENE-1-CARBOXALDEHYDE

Reaction:

Procedure:

A slurry containing 360 grams of allyl chloride; 180 grams of flake sodium hydroxide; 400 ml of toluene; 25 grams of Aliquat 336 ® (registered trademark of General Mills Chemicals Inc. of Minneapolis, Minn., which identifies tricapryl methyl ammonium chloride); and 576 grams of a mixture of 4-(4-methyl-3-pentenyl)-3-cyclohexene-1-carboxaldehyde and 3-(4-methyl-3-pentenyl)-3-cyclohexene-1-carboxaldehyde is heated at reflux for 4 hours. Water is added to the cooled reaction mass and the resulting organic phase is separated and washed twice with water. Distillation through a short column affords an oil which contains 308 grams (42% yield) of product (b.p. 145° C, 1.1 mm Hg). The product is purified by steam vacuum fractional distillation through a 1 × 12 inches Goodloe-packed column (b.p. 123°–127° C, 2.0 mm Hg at a steam rate of 1.6 ml liq. $H_2O$/min).

Figure 1:
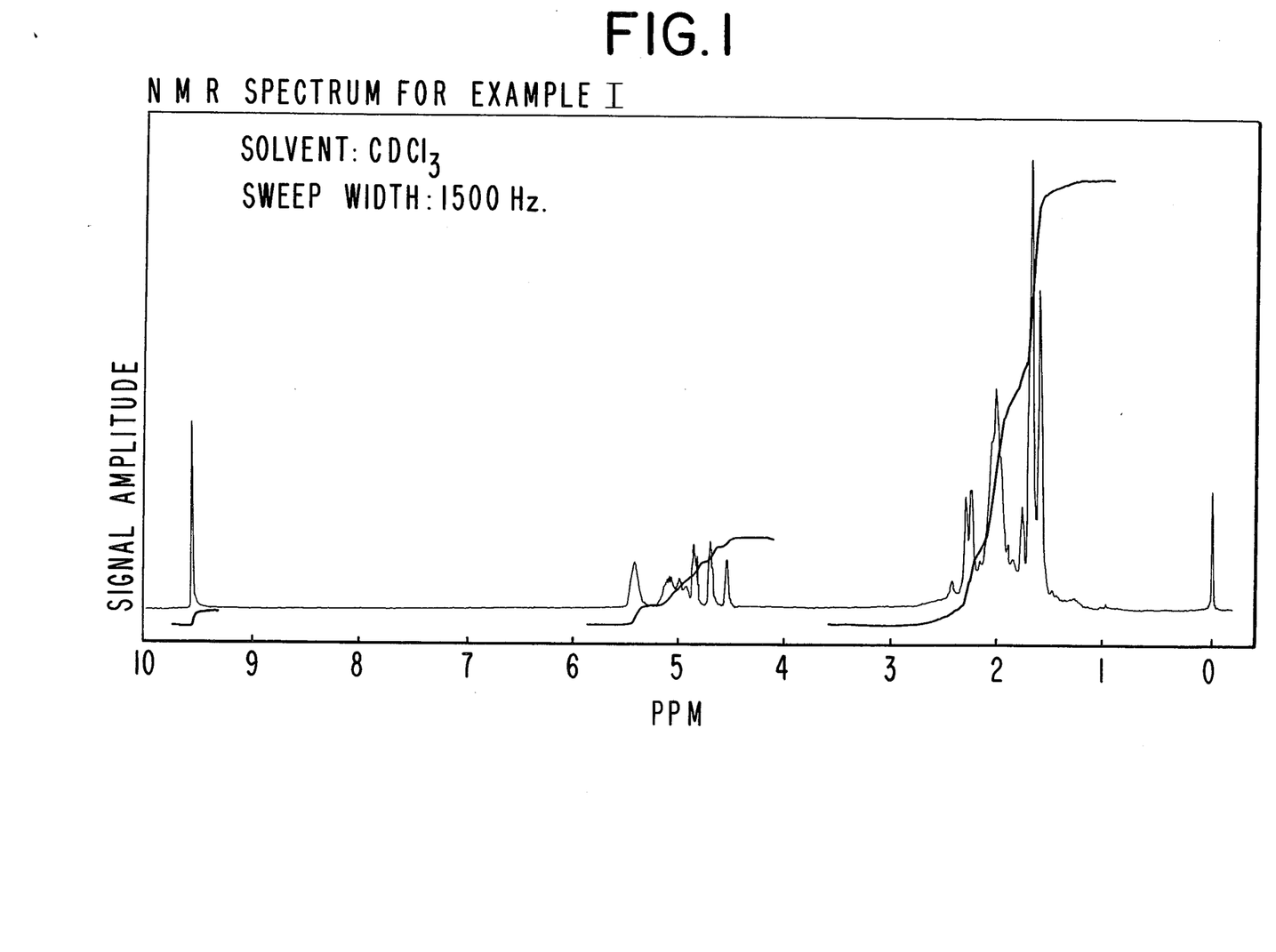
FIG. 1 represents the NMR spectrum for the 1-(2-methyl-2-propenyl)-(4-methyl-3-pentenyl)-Δ³-cyclohexene-1-carboxaldehydes produced according to Example I.

The NMR spectrum for the reaction product produced herein is set forth in FIG. 1.

Figure 2:
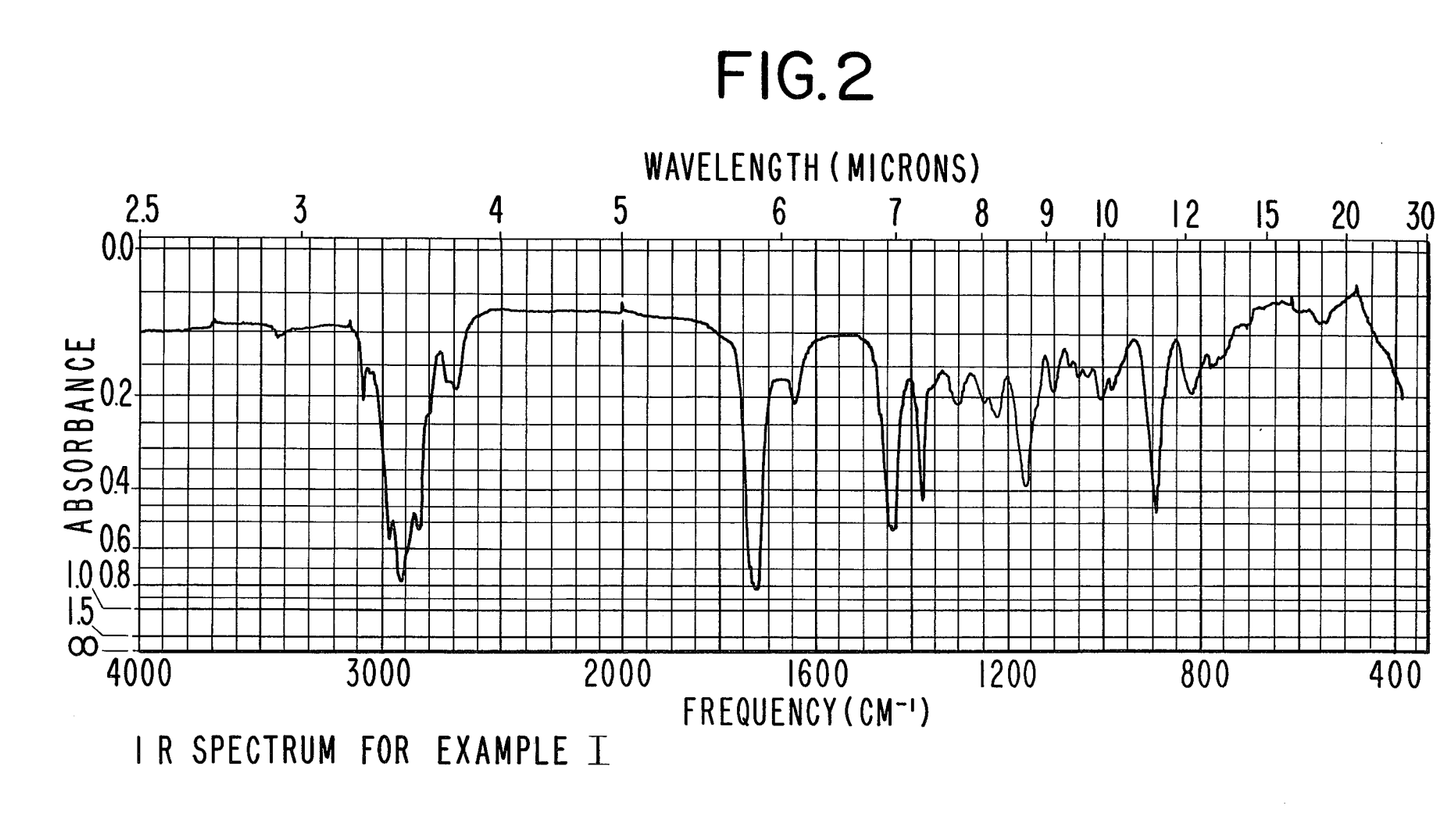
FIG. 2 represents the Infrared spectrum for the 1-(2-methyl-2-propenyl)-(4methyl-3-pentenyl)-Δ³-cyclohexene-1-carboxaldehydes produced according to Example I.

The Infrared spectrum is set forth in FIG. 2.

EXAMPLE II

A perfume composition is prepared by admixing the following ingredients in the indicated proportions:

| Ingredient | Amount (Grams) |
| --- | --- |
| n-Decyl Aldehyde | 1 |
| n-Dodecyl Aldehyde | 2 |
| Methyl Nonyl Acetaldehyde | 0.5 |
| Linalool | 50 |
| Linalyl Acetate | 70 |
| Phenyl Ethyl Alcohol | 100 |
| Petigrain SA | 20 |
| Bergamot Oil | 30 |
| Alpha Methyl Ionone | 25 |
| A mixture of the 1-(2-methyl-2-propenyl)-(4-methyl-3-pentenyl)- $\Delta^3$-cyclohexene-1-carboxaldehydes, produced according to Example I | 10 |
| Cyclized Bicyclo C-12 material produced according to the process of Example IV of Canadian Patent 854,225, issued on October 20, 1970 | 5 |
| Isobornyl cyclohexyl alcohol | 10 |
| Benzyl Acetate | 25 |
| 2-n-Heptyl cyclopentanone | 5 |
| | 353.3 (TOTAL) |

The foregoing blend is evaluated and found to have a high degree of richness and persistence in its novel natural fruity quality. This base composition can be admixed with aqueous ethanol, chilled and filtered to produce a finished cologne. The cologne so prepared has a fruity and floral aroma leaning towards a lavender-like note. The base composition can also be used to scent soap or other toilet goods such as lotion, aerosol, sprays and the like.

EXAMPLE III

PREPARATION OF A COSMETIC POWDER COMPOSITION

A cosmetic powder is prepared by mixing in a ball mill, 100 g of talcum powder with 0.25 g of the 1-(2-methyl-2-propenyl)-(4-methyl-3-pentenyl)-$\Delta^3$-cyclohexene-1-carboxaldehyde(s) produced according to Example I. It has excellent citrus/fruity and floral nuances.

EXAMPLE IV

PERFUMED LIQUID DETERGENT

Concentrated liquid detergents with fruity, lavender-like notes and citrus/fruity and floral nuances (which detergents are produced from Lysine salt of n-dodecyl benzene sulfonic acid as more specifically described in U.S. Pat. No. 3,948,818, issued on Apr. 6, 1976) are prepared containing the 1-(2-methyl-2-propenyl)-(4-methyl-3-pentenyl)-$\Delta^3$-cyclohexene-1-carboxaldehyde(s) prepared according to Example I. They are prepared by adding and homogeneously mixing the appropriate quantity of the 1-(2-methyl-2-propenyl)-(4-methyl-3-pentenyl)-$\Delta^3$-cyclohexene-1-carboxaldehyde(s) in the liquid detergent. The detergents all possess a fruity/citrus note, the intensity increasing with greater concentrations of the 1-(2-methyl-2-propenyl)-(4-methyl-3-pentenyl)-$\Delta^3$-cyclohexene-1-carboxaldehyde(s).

EXAMPLE V

PREPARATION OF A COLOGNE AND HANDKERCHIEF PERFUME

The 1-(2-methyl-2-propenyl)-(4-methyl-3-pentenyl)-$\Delta^3$-cyclohexene-1-carboxaldehyde(s), prepared according to the process of Example I is incorporated in a cologne at a concentration of 2.5% in 85% aqueous ethanol; and into a handkerchief perfume at a concentration of 20% (in 95% aqueous ethanol). A distinct and definite citrus/fruity, floral and spicey nuance is imparted to the cologne and to the handkerchief perfume.

EXAMPLE VI

PREPARATION OF A COLOGNE AND HANDKERCHIEF PERFUME

The composition of Example II is incorporated in a cologne at a concentration of 2.5% in 85% aqueous ethanol; and into a handkerchief perfume at a concentration of 20% (in 85% aqueous ethanol). The use of the 1-(2-methyl-2-propenyl)-(4-methyl-3-pentenyl)-$\Delta^3$-cyclohexene-1-carboxaldehyde(s) in the composition of Example II affords a distinct and definite fruity/citrus nuance to the handkerchief perfume and cologne.

EXAMPLE VII

PREPARATION OF SOAP COMPOSITION

One hundred grams of soap chips are mixed with 2 grams of the composition of Example II until a substantially homogeneous composition is obtained. The perfumed soap composition manifests an excellent fruity/citrus and floral nuance.

EXAMPLE VIII

PREPARATION OF A DETERGENT COMPOSITION

A total of 100 grams of a detergent powder (Lysine salt of n-dodecyl benzene sulfonic acid as more specifically described in U.S. Pat. No. 3,948,818, issued on Apr. 6, 1976) are mixed with 0.70 grams of the composition of Example II until a substantially homogeneous composition is obtained. This composition has an excellent fruity/citrus and floral nuance.

EXAMPLE IX

TOBACCO FORMULATION

A tobacco mixture is produced by admixing the following ingredients:

| Ingredients | Parts by Weight |
| --- | --- |
| Bright | 40.1 |
| Burley | 24.9 |
| Maryland | 1.1 |
| Turkish | 11.6 |
| Stem (flue-cured) | 14.2 |
| Glycerine | 2.8 |
| Water | 5.3 |

Cigarettes are prepared from this tobacco.
The following flavor formulation is prepared:

| Ingredients | Parts by Weight |
| --- | --- |
| Ethyl butyrate | .05 |
| Ethyl valerate | .05 |
| Maltol | 2.00 |
| Cocoa extract | 26.00 |
| Coffee extract | 10.00 |
| Ethyl alcohol | 20.00 |
| Water | 41.90 |

The above-stated tobacco flavor formulation is applied at the rate of 1.0% to all of the cigarettes produced using the above tobacco formulation. Half of the cigarettes are then treated with 500 or 1,000 ppm of the mixture produced according to Example I of 1-methallyl-3 and 4-(4-methyl-3-pentenyl)-$\Delta^3$-cyclohexene-1-carboxaldehyde(s). The control cigarettes not containing the mixture of 1-methallyl-3 or 4-(4-methyl-3-pentenyl)-$\Delta^3$-cyclohexene-1-carboxaldehyde(s) produced according to the process of Example I and the experimental cigarettes which contain the mixture of 1-methallyl-3 or 4-(4-methyl-3-pentenyl)-$\Delta^3$-cyclohexene-1-carboxaldehyde(s) produced according to the process of Example I are evaluated by paired comparison and the results are as follows:

The experimental cigarettes are found to have more smoke body and a fuller smoke body sensation in the mouth on smoking. The tobacco-like notes are enhanced and the flavor of the tobacco on smoking is more aromatic with spicey/coriander-like notes.

All cigarettes are evaluated for smoke flavor with a 20 mm cellulose acetate filter.

EXAMPLE X

A slurry containing 289 grams of methallyl chloride; 252 grams of flaked potassium hydroxide; 400 ml of toluene; 40 grams of 18-crown-6 having the structure:

and 576 grams of myrac aldehyde is heated at reflux for 3 hours. The reaction mass is treated as in Example I to yield a mixture of compounds having the structures:

EXAMPLE XI

A slurry containing 289 grams of methallyl bromide; 180 grams of granular sodium hydroxide; 400 ml of toluene; 40 grams of triethylamine; and 576 grams of a mixture of myrac aldehyde is heated at reflux for 8 hours. The reaction mass is treated as in Example I to afford a mixture of compounds having the structures:

What is claimed is:

1. A mixture of the compounds 1-(2-methyl-2-propenyl)-3-(4-methyl-3-pentenyl)-$\Delta^3$-cyclohexene-1-carboxaldehyde and 1-(2-methyl-2-propenyl)-4-(4-methyl-3-pentenyl)-$\Delta^3$-cyclohexene-1-carboxaldehyde defined by the structure:

wherein the carboxaldehyde moiety is bonded either at the alpha-carbon atom or the beta-carbon atom of the cyclohexenyl moiety.

2. A compound having the structure:

3. A compound having the structure:

* * * * *